(12) United States Patent
Vivier et al.

(10) Patent No.: US 9,687,471 B2
(45) Date of Patent: *Jun. 27, 2017

(54) STABILIZED ASCORBIC ACID SOLUTIONS; METHOD OF USE THEREOF; PROCESS FOR THEIR OBTENTION; AND COMPOSITIONS COMPRISING THE SAME

(71) Applicant: VIVIER CANADA INC., Vaudreuil-Dorion (CA)

(72) Inventors: Ghislain Vivier, St-Lazare (CA); Anthony Costa, Vimont (CA)

(73) Assignee: VIVIER CANADA INC., Vaudreuil-Dorion (CA)

( * ) Notice: Subject to any disclaimer, the term of this patent is extended or adjusted under 35 U.S.C. 154(b) by 685 days.

This patent is subject to a terminal disclaimer.

(21) Appl. No.: 14/167,012

(22) Filed: Jan. 29, 2014

(65) Prior Publication Data

US 2014/0148509 A1    May 29, 2014

Related U.S. Application Data

(63) Continuation of application No. 13/227,838, filed on Sep. 8, 2011, now abandoned, which is a continuation of application No. 12/019,991, filed on Jan. 25, 2008, now Pat. No. 8,053,469, which is a continuation of application No. 10/363,929, filed on Mar. 7, 2003, now Pat. No. 7,342,045, which is a continuation-in-part of application No. PCT/CA01/01270, filed on Sep. 10, 2001.

(60) Provisional application No. 60/231,068, filed on Sep. 8, 2000.

(51) Int. Cl.
| | | |
|---|---|---|
| A61K 31/375 | (2006.01) | |
| A61K 8/34 | (2006.01) | |
| A61K 8/67 | (2006.01) | |
| A61K 36/752 | (2006.01) | |
| A61Q 19/00 | (2006.01) | |
| A61Q 17/04 | (2006.01) | |
| A61Q 19/08 | (2006.01) | |

(52) U.S. Cl.
CPC ............. *A61K 31/375* (2013.01); *A61K 8/34* (2013.01); *A61K 8/345* (2013.01); *A61K 8/676* (2013.01); *A61K 36/752* (2013.01); *A61Q 19/00* (2013.01); *A61K 2800/52* (2013.01); *A61Q 17/04* (2013.01); *A61Q 19/08* (2013.01)

(58) Field of Classification Search
None
See application file for complete search history.

(56) References Cited

U.S. PATENT DOCUMENTS

| | | |
|---|---|---|
| 4,983,382 A | 1/1991 | Wilmott |
| 5,093,360 A | 3/1992 | Yu |
| 5,140,043 A | 8/1992 | Darr |
| 5,736,567 A | 4/1998 | Cantin |
| 5,827,520 A | 10/1998 | De Salvert |
| 5,869,063 A | 2/1999 | Lezdey |
| 5,935,584 A | 8/1999 | Guerrero |
| 5,972,360 A | 10/1999 | Braun |
| 6,087,393 A | 7/2000 | Mathur |
| 6,103,267 A | 8/2000 | Mitchnick |
| 6,124,348 A | 9/2000 | Wells |
| 6,284,234 B1 | 9/2001 | Niemiec |
| 7,342,045 B2 | 3/2008 | Vivier et al. |
| 8,053,469 B2 | 11/2011 | Vivier et al. |

FOREIGN PATENT DOCUMENTS

| | | |
|---|---|---|
| DE | 100 09 252 | 9/2001 |
| EP | 0 770 381 | 5/1997 |
| EP | 0 884 045 | 12/1998 |
| WO | WO 98/23152 | 6/1998 |

OTHER PUBLICATIONS www.mayoclinic.com/health/dermatitis-eczema/DS00339/DSECTION=prevention—accessed May 2012.*
http://beauty.ivillage.com/skinbody/facecare/0,,rf9x-p,00.html—accessed May 2008.*
Database Embase Online; Elsevier Science Publishers, Amsterdam, NL; retrieved from STN Database accession No. 77048093; XP002198232, 1976.

* cited by examiner

*Primary Examiner* — Susan Hoffman
(74) *Attorney, Agent, or Firm* — Julie Gauvreau

(57) ABSTRACT

This invention relates to improved solutions comprising ascorbic acid (vitamin C). These solutions may comprise as much as 15% ascorbic acid; they are stable for at least two years, without no significant development of yellowish coloration and no substantial (not more than 10%) degradation of the vitamin. The process involves sequential additions of ascorbic acid and ethoxydiglycol to a first solution of vitamin in water, which are followed by addition of propylene glycol. The stirring speed that occurs during the additions favors a process of micronization. Mild heating is used to achieve ascorbic acid concentrations equivalent to about 6% in 10% water or higher.

30 Claims, 2 Drawing Sheets

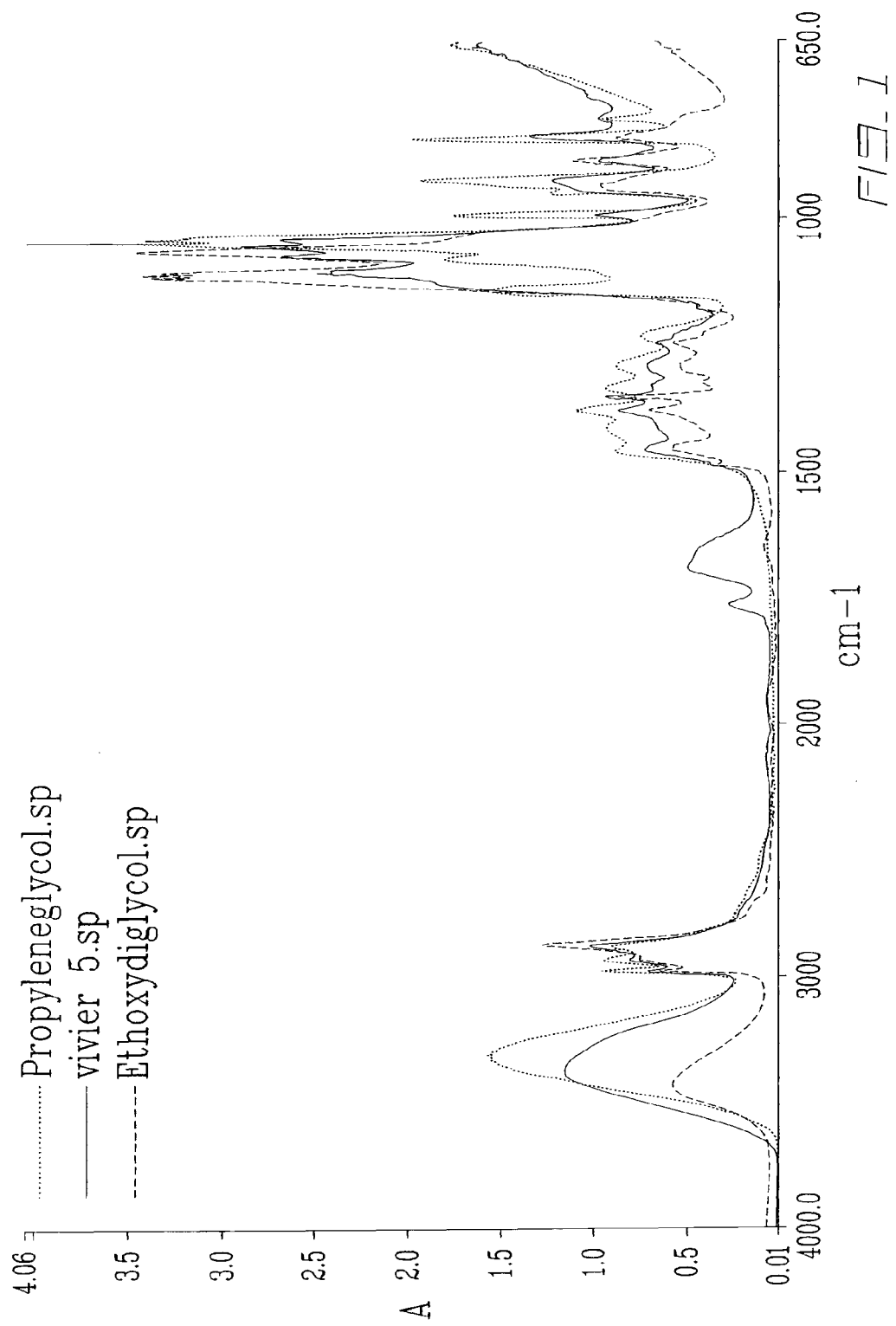

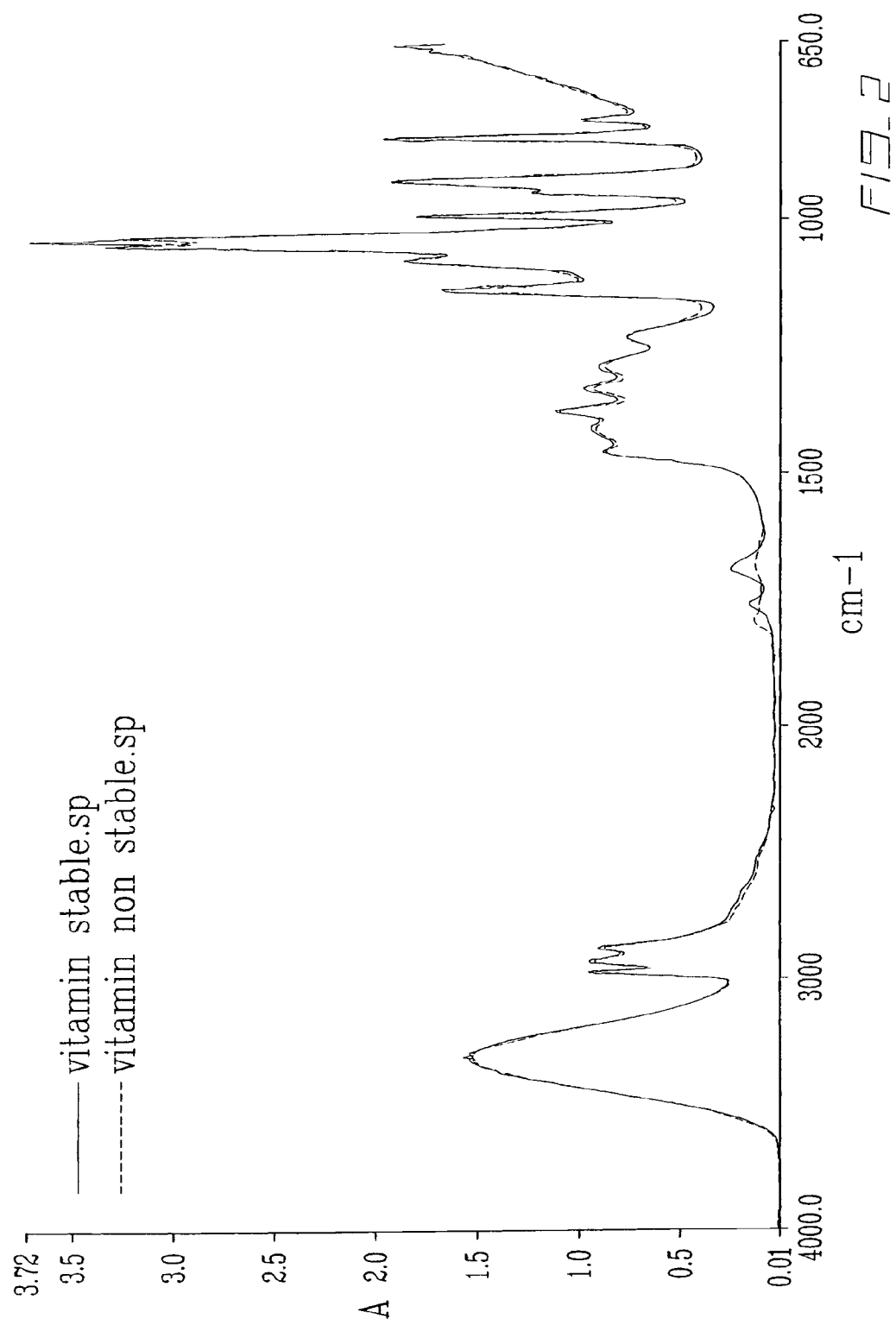

STABILIZED ASCORBIC ACID SOLUTIONS; METHOD OF USE THEREOF; PROCESS FOR THEIR OBTENTION; AND COMPOSITIONS COMPRISING THE SAME

CROSS-REFERENCE TO RELATED APPLICATIONS

This application is a Continuation Application of U.S. patent application Ser. No. 13/227,838, which is a Continuation Application of U.S. patent application Ser. No. 12/019,991 now U.S. Pat. No. 8,053,469 issued on Nov. 8, 2011, which is a Continuation Application of U.S. patent application Ser. No. 10/363,929 now U.S. Pat. No. 7,342,045 issued on Mar. 11, 2008, which is a Continuation-in-Part Application of PCT application no PCT/CA01/01270 filed on Sep. 10, 2001 and published in English under PCT Article 21(2), which itself claims priority on U.S. provisional application No. 60/231,068, filed on Sep. 8, 2000. All documents above are incorporated herein in their entirety by reference.

FIELD OF THE INVENTION

The present invention relates to stabilized ascorbic acid solutions; method of use thereof; and compositions comprising the same. This invention further relates to processes for the obtention of such stabilized ascorbic acid solutions and compositions.

BACKGROUND OF THE INVENTION

Skin appearance and elasticity has always been a cosmetic concern for almost everybody. Skin protection against actinic radiations has become a great health concern over the past ten to twenty years. UV exposure results in the formation of noxious reactive oxygen species (ROS). Skin damages cannot only be life threatening, but they contribute for premature skin ageing. The most popular way by which UV damages are prevented is to block their penetration through the skin using sunscreen formulations. The notion that antioxidants may also be used to improve the therapeutic or cosmetic performance of dermatological formulations is more recent. Antioxidants would in that case have a role in neutralizing ROS or preventing their formation into the skin. Antioxidants include compounds such as ascorbic acid and complexes, tocopherol, tocopheryl acetate, retinol, retinyl palmitate, hydroquinone, proanthocyaniadins, butylated hydroxytoluene, butylated hydroxyanisole, astaxanthin, alpha lipoic acid, tocotrienols, certain proteins and coenzyme Qio. Each antioxidant may be used alone or in combination with each another as active ingredients or as stabilizing and preservation agents to protect other active ingredients against oxidative damages. Antioxidants may also be used alone or in combination with reducing agents such as L-cysteine or glutathione.

Antioxidants need to remain in their unoxidized form in order to be efficacious against ROS. Maintenance of antioxidants stability in solutions has been a challenge over the past years.

Ascorbic acid, also known as vitamin C, is certainly one of the most popular antioxidants. This vitamin is known for its general essential role in maintaining health. In dermatology, vitamin C is known for its implication in collagen synthesis as well as for its antioxidant function, which ultimately helps reduce the expression of skin ageing, translated into the appearance of fine lines or wrinkles in the skin. Vitamin C also has an anti-tyrosinase effect on the skin for skin whitening effect.

Vitamin C is a moderately strong reducing agent, which makes it unstable in aqueous solutions, especially at high pHs. It is particularly subject to oxidative degradation.

Water is one of the best solvents to dissolve ascorbic acid. Its limit of solubility appears to be about 330 mg/ml in water. Ascorbic acid is therefore relatively soluble in water. It is much less soluble in glycols such as propylene glycol (50 mg/ml) and in alcohols such as ethanol (10 mg/ml in absolute ethanol).

Although water is the best solvent to provide an ascorbic acid solution, it is paradoxically one of the worst to protect ascorbic acid against oxidative damages. A proportion of water needs to be replaced with another solvent that provides more stability.

The problem to be solved with ascorbic acid formulations has always been to find a compromise between solubilization and stability.

U.S. Pat. No. 5,140,043 discloses an ascorbic acid formulation that has a pH below 3.5, preferably below 2.5. A low pH insures that a high proportion of ascorbic acid remains in the protonated, uncharged form. The protonated form is more stable and more easily permeant through skin and mucosae membranes than the non-protonated counterpart. Metals also negatively influence the preponderance of the protonated form of ascorbic acid in a solution. A chelator may therefore be added in ascorbic acid solutions to stabilize the vitamin. The carrier in which the ascorbic acid is dissolved comprises an alkylene glycol, namely propylene glycol. The carrier further comprises hydroxyalkylcellulose, the polyhydroxyl function of which apparently participates in the typical reactions of alcohols. The proportion of water remains very high (more than 50% by weight), which may lead to a relatively rapid degradation at room temperature.

U.S. Pat. No. 4,983,382 discloses the use of polyhydric liquids to solubilize and stabilize ascorbic acid. A mixture of ethanol 55-65% and propylene glycol 20-25% is especially preferred for its excellent cosmetic properties. Water may be present in concentrations up to 12% without adversely affecting the stability of ascorbic acid solubilized in a mixture of alcohol and propylene glycol. The organic solvents, all combined, represent up to 90% by weight of a composition. The low water contents recommended does not appear to permit solubilization of more than 10% of ascorbic acid.

U.S. Pat. No. 6,124,348 proposes to combine ascorbic acid, a volatile organic solvent such as isodecane and a gelling base. The solvent does not react with or solubilize the vitamin. Such a suspension is applied to the skin. The skin moisture penetrates the suspension and solubilizes the ascorbic acid which then can permeate the skin layer. The solubility of ascorbic acid in the formulation is not dealt with in this patent.

Another type of dispersion of ascorbic acid is disclosed in U.S. Pat. No. 6,103,267. Again, this patent does not describe a solution of ascorbic acid.

Another approach to stabilize ascorbic acid solution has been to decrease water activity in the same. U.S. Pat. No. 5,736,567 discloses compositions wherein water activity is decreased below 0.85. The lowest water activity achieved with the descriptive examples has been 0.63. At this value, the water content is 21%, the ascorbic acid concentration is 3%, the polypropylene glycol content is 39.4% and polyethylene glycol content is 13% (all percentages given by weight of formulation). The aqueous phase is combined with an oil phase to provide a composition that has a "structure". This particular formulation has been tested for its stability. After two months at 20° C., 0.7% of ascorbic acid has degraded which is fairly good compared to the same solution prepared with 28% water (3.5% degradation) and a composition also comprising 28% water but without the glycols (6.2% degradation). The concentration of ascorbic acid that may be present in these formulations is not higher than 10%.

U.S. Pat. No. 6,087,393 discloses a composition comprising ascorbic acid in a mixed glycerol carrier. The glycerol carrier comprises propylene glycol and butylene glycol, as well as a stabilizer which may be diethylene glycol monoethylether. The preferred proportions of propylene glycol, butylene glycol and diethylene glycol monoethylether are 25-80%, 5-30% and 5-10%, respectively. Ascorbic acid may be present in concentrations comprised between 2% and 15%. In these solutions, the major glycol component is clearly propylene glycol while butylene glycol is added as a solubilizing aid and diethylene glycol monoethylether is added in minor proportion as a stabilizer. The stability of these solutions is not excellent because, at best, the samples admittedly start to develop a yellowish colour after one month at room temperature.

Another approach to formulate and use ascorbic acid in dermatology has been not to deal with its stability. U.S. Pat. No. 5,935,584 proposes to provide separate compartments that are extemporaneously mixed together prior to use. One compartment comprises vitamin C, the other one comprises an aqueous phase. Once reconstituted by admixing the contents of both compartments, ascorbic acid is provided in a solution that is more alkaline than usual solutions of ascorbic acid. The limit of solubility of the vitamin achieved with such a solution is close to 50%. Further, once reconstituted, the ascorbic acid formulation comprises about half-and-half polyethylene glycol and water.

In view of the foregoing, there is still a need to develop a solubilized ascorbic acid in suitable concentrations, and which remains stable for a practical shipping and storage amount of time, and which keeps a clear substantially non-coloured visual aspect for the same amount of time.

SUMMARY OF THE INVENTION

It is a first goal of this invention to provide a solution of ascorbic acid that is stable at least for about twenty-four months. The solution may comprise concentrations of ascorbic acid as high as 5 to 15%.

The solution comprises a carrier essentially formed of water, ethoxydiglycol and propylene glycol. Ethoxydiglycol is the major glycol component. The solution may be used as is or combined to other carriers to provide a plurality of different topical formulations or compositions. Sprays, emulsions, droplets, creams, ointments, milks and lotions are all examples of suitable compositions. The solutions and compositions may be used to prevent or treat a disease or disorder caused by ROS, namely consequent to U.V. or sun exposure. They may further include an anti-oxidant or a reducing agent and they may also include sun blocking ingredients, and depigmentation (skin whitening) agents or other cosmetically valuable compounds. Compositions comprising the present vitamin C solution and one or more of an α-hydroxy acid, retinol, kojic acid, hydroquinone, wine extracts kinetin, vitamin K, ascorbyl palmitate, and magnesium and sodium ascorbyl phosphate are all examples of specific cosmetic compositions which are objects of this invention.

It is another object of this invention to provide a process by which such a stable vitamin C solution can be obtained, which involves sequential additions of vitamin and ethoxydiglycol, followed by propylene glycol, under high stirring speed. If needed, a last addition of ascorbic acid and heating steps are performed to achieve high concentrations of the vitamin. The high stirring speed provides for micronization of the components, which is responsible for the stability of the solutions.

As used herein, the terminology "anti-oxidant plant extract" is meant to refer to plant, seed, herb, spice or fruit extract.

More particularly, there is provided a process for obtaining a stabilized ascorbic acid of a desired concentration of 15% (w/w) or less in solution, which comprises dissolving a first amount of ascorbic acid in water, thereby obtaining a first solution; adding a first amount of ethoxydiglycol to said first solution, under high stirring speed to micronize ethoxydiglycol, ascorbic acid and water, thereby obtaining a second solution; adding a second amount of ascorbic acid to said second solution under high stirring speed, thereby obtaining a third solution; adding a second amount of ethoxydiglycol to said third solution under high stirring speed, thereby obtaining a fourth solution; and adding propylene glycol, which results into the obtention of a solution of ascorbic acid having substantially the desired concentration.

In a specific embodiment, there is provided a process of the present invention, which further comprises a step f) of adding a anti-oxidant plant extract to the solution of step e).

In another specific embodiment, there is provided a process of the present invention, wherein said first and second amounts of ascorbic acid achieve a concentration of 3% and 2% respectively, said first and second amounts of ethoxydiglycol are both 27.35%, propylene glycol and water are added to achieve 29% and 10%, respectively, and said anti-oxidant plant extract achieves a concentration of 1%, the percentages being given by weight of the final solution.

In another specific embodiment, there is provided a process of the present invention, which further comprises adding a fragrance material to the solution obtained after step f).

In another specific embodiment, there is provided a process of the present invention, which further comprises the steps of adding a third amount of ascorbic acid between steps d) and e).

In another specific embodiment, there is provided a process of the present invention, which, when the desired concentration of ascorbic acid is more than 6% (w/w), further comprises a step of adding a fourth amount of ascorbic acid after step f), followed by a step of heating at a temperature of about 37 to 42° C. until a clear solution is obtained, followed by a step of cooling down to room temperature.

In another specific embodiment, there is provided a process of the present invention, wherein said temperature is 40° C.

In another specific embodiment, there is provided a process of the present invention, wherein said first, second, third and fourth amounts of ascorbic acid are 3%, 1.5%, 3.5% and 2%, respectively.

In another specific embodiment, there is provided a process of the present invention, wherein said first and second amounts of ethoxydiglycol are added to achieve both 25.85%, said propylene glycol, water and anti-oxidant plant extract are added to achieve 27%, 10%, and 1%, respectively, the percentages being given by weight of the final solution.

In another specific embodiment, there is provided a process of the present invention, wherein said first and second amounts of ethoxydiglycol are added to achieve both 24.45%, said propylene glycol, water and anti-oxidant plant extract are added to achieve 26%, 10%, and 1%, respectively, and hydroquinone is added to achieve 2% after the step of cooling down to room temperature, the percentages being given by weight of the final solution.

In another specific embodiment, there is provided a process of the present invention, wherein said first and second amounts of ethoxydiglycol are added to achieve 23.45%, said propylene glycol, water and anti-oxidant plant extract are added to achieve 26%, 10%, and 1%, respectively, and hydroquinone is added to achieve 4% after the step of cooling down to room temperature, the percentages being given by weight of the final solution.

In another specific embodiment, there is provided a process of the present invention, wherein said first and second amounts of ethoxydiglycol are added to achieve both 25.935%, said propylene glycol, water and anti-oxidant plant extract are added to achieve 27%, 10%, and 1%, respectively, and kinetin is added to achieve 0.03% after the step of cooling down to room temperature, the percentages being given by weight of the final solution.

In another specific embodiment, there is provided a process of the present invention, wherein said first, second, third and fourth amounts of ascorbic acid are 4.5%, 2.25%, 5.25% and 3%, respectively, said first and second amounts of ethoxydiglycol are both 23.4%, propylene glycol and water are added to achieve 22% and 15%, respectively, and said anti-oxidant plant extract achieves a concentration of 0.9%, the percentages being given by weight of the final solution.

In another specific embodiment, there is provided a process of the present invention, which comprises adding a fragrance material of 0.3% after the cooling down step.

In accordance with another aspect of the present invention, there is provided a solution which comprises more than zero and up to 15% L-ascorbic acid in a carrier comprising 10 to 15% water, 46.8 to 54.7% ethoxydiglycol, 22 to 29% propylene glycol, all percentages given by weight of final composition, the balance to 100% comprising a percentage of at least one anti-oxidant agent.

In a specific embodiment, there is provided a solution of the present invention, wherein the at least one anti-oxidant agent comprises an anti-oxidant plant extract.

In a specific embodiment, there is provided a solution of the present invention, wherein the anti-oxidant plant extract is a grapefruit plant extract.

In a specific embodiment, there is provided a solution of the present invention, further comprising an additional anti-oxidant selected from the group consisting of kinetin and hydroquinone.

In a specific embodiment, there is provided a solution of the present invention, further comprising a fragrance material, which has the following composition: —water 10%; —L-ascorbic acid 5%; —ethoxydiglycol 54.7%; —propylene glycol 29%; —anti-oxidant plant extract 1%; and—fragrance material 0.3%, all percentages given by weight of final composition.

In a specific embodiment, there is provided a solution of the present invention, further comprising a fragrance material, which has the following composition:

| water | 10%; |
| L-ascorbic acid | 10%; |
| ethoxydiglycol | 51.7%; |
| propylene glycol | 27%; |
| anti-oxidant plant extract | 1%; and |
| fragrance material | 0.3%, | all percentages given by weight of final composition.

In a specific embodiment, there is provided a solution of the present invention, further comprising a fragrance material, which has the following composition:

| water | 15%; |
| L-ascorbic acid | 15%; |
| ethoxydiglycol | 46.8%; |
| propylene glycol | 22%; |
| anti-oxidant plant extract | 0.9%; and |
| fragrance material | 0.3%, | all percentages given by weight of final composition.

In a specific embodiment, there is provided a solution of the present invention, further comprising a fragrance material and hydroquinone, which has the following composition:

| water | 12%; |
| L-ascorbic acid | 10%; |
| ethoxydiglycol | 48.90%; |
| propylene glycol | 26%; |
| anti-oxidant plant extract | 1%; |
| fragrance material | 0.1%; and |
| hydroquinone | 2%, | all percentages given by weight of final composition.

In a specific embodiment, there is provided a solution of the present invention, further comprising a fragrance material and hydroquinone, which has the following composition:

| water | 12%; |
| L-ascorbic acid | 10%; |
| ethoxydiglycol | 46.90%; |
| propylene glycol | 26%; |
| anti-oxidant plant extract | 1%; |
| fragrance material | 0.1%; and |
| hydroquinone | 4%, | all percentages given by weight of final composition.

In another specific embodiment, there is provided a solution of the present invention, further comprising a fragrance material and kinetin, which has the following composition:

| water | 10%; |
| L-ascorbic acid | 10%; |
| ethoxydiglycol | 51.87%; |
| propylene glycol | 27%; |
| anti-oxidant plant extract | 1%; |
| fragrance material | 0.1%; and |
| kinetin | 0.03%, | all percentages given by weight of final composition.

In another specific embodiment, there is provided the solution of the present invention, further comprising a topically suitable carrier or compound.

In accordance with another aspect of the present invention, there is provided a topical composition comprising the solution of the present invention, and a topically suitable carrier or compound.

In another specific embodiment of the solution of the present invention, said topically suitable carrier or compound is selected from the group consisting of tocopherol, tocopheryl acetate, retinol, retinyl palmitate, hydroquinone, proanthocyanidins, butylated hydroxytoluene, butylated hydroxyanisole, astaxanthin, alpha lipoic acid, tocotrienols, coenzyme Q10, α-hydroxy acid, kojic acid, kinetin, wine extract, vitamin K, ascorbyl palmitate, magnesium ascorbyl phosphate, sodium ascorbyl phosphate, a sun blocking agent and any combination thereof.

In accordance with another aspect of the present invention, there is provided a method for preventing or treating a disease or disorder involving or caused by reactive oxygen species, which comprises the step of topically administering a suitable amount of the solution of the present invention.

In another specific embodiment of the method of the present invention, said reactive oxygen species are caused by U.V or sun exposure.

BRIEF DESCRIPTION OF THE DRAWINGS

This invention will be described herein below by reference to the following preferred embodiments and appended figures which purpose is to illustrate rather than to limit its scope.

In the appended drawings:

FIG. 1 represents superimposed chromatograms of the present solution (5% ascorbic acid) and of the two glycols composing the carrier.

FIG. 2 represents comparative chromatograms of the solution of the present invention and a solution of vitamin C submitted to a controlled degradation.

DETAILED DESCRIPTION OF SPECIFIC EMBODIMENTS OF THE INVENTION

This process comprises the step of dissolving a first quantity of ascorbic acid in 10% water, which is followed by addition of a first quantity of ethoxydiglycol, under high stirring speed. The step of adding ascorbic acid and ethoxydiglycol can be repeated numerous times (at least one other time), depending on the concentration of ascorbic acid that is sought. After sequential additions of second or third quantities of ascorbic acid and ethoxydiglycol, propylene glycol is added to contribute, with water, in the solubilization of ascorbic acid. The rapid agitation and the presence of ethoxydiglycol after each sequential addition of ascorbic acid provide for a micronized and stabilized solution.

When concentrations of ascorbic acid higher than about 6% are needed, a mild heating step (at least about 37-42° C., preferably 40° C.) is required to solubilize the last added quantities of vitamin, in the presence of propylene glycol. For formulating the highest vitamin C concentration of 15%, the concentration of water is increased from 10% to 15%. In such a case, sequential additions of ascorbic acid and ethoxydiglycol may achieve a concentration such that a higher concentration is achieved (12% again in the presence of propylene glycol) prior to heating. A last addition of vitamin can be made, followed by a last heating step. Upon cooling at room temperature, the solution remains stable.

The selection of the right solvents which involves particularly a high concentration of ethoxydiglycol, and of the right sequential additions of ascorbic acid, ethoxydiglycol and propylene glycol, combined to a high speed that allows micronization of ascorbic acid into such a solution, all contribute to obtaining a stable solution of ascorbic acid. Heat contributes to increasing the amount of solubilized ascorbic acid.

A micronization process appears to result in a product wherein the contact of oxygen with the vitamin, is sharply reduced once the latter is in solution. This reduces the oxidative damages to the precious vitamin. The process provides for a solution that has a shelf life of at least about two years, without any substantial development of yellowish colour, which is without any precedent (Data not shown).

Formulations for the Vitamin-C 5%, −10% and 15% according to specific embodiments are as follows:

| Item | Ingredient | 5% % w/w | 10% % w/w | 15% % w/w | 10% % w/w | 10% % w/w | 10% % w/w |
|---|---|---|---|---|---|---|---|
| 1. | Demineralized water grade USP | 10.0 | 10.0 | 15.0 | 12.0 | 12.0 | 10.0 |
| 2. | L-Ascorbic Acid grade USP | 5.0 | 10.0 | 15.0 | 10.0 | 10.0 | 10.0 |
| 3. | Ethoxydiglycol grade USP | 54.7 | 51.7 | 46.8 | 48.90 | 46.90 | 51.88 |
| 4. | Anti-oxidant agent | 1.0 | 1.0 | 0.9 | 1.0 | 1.0 | 1.0 |
| 5. | Propylene Glycol grade SUP | 29.0 | 27.0 | 22.0 | 26 | 26.0 | 27.0 |
| 6. | Fragrance material grade MFR | 0.30 | 0.30 | 0.30 | 0.10 | 0.10 | 0.10 |
| 7. | Hydroquinone grade USP | | | | 2.0 | 4.0 | |
| 8. | Kinetin grade MFR | | | | | | 0.03 |

Item 6 appears optional, since it is a fragrance that is added to confer more attractive properties to the solution for the consumer. In specific embodiments presented in the examples below, Apple Crunch™ was used as fragrance material because of its availability on the market. Other fragrance may be used such as Apple Fresh™. Item 4 is used as an anti-oxidant. Items 7 and 8 are further anti-oxidants used in specific embodiments.

General Manufacturing Procedure

The following sequence has been adopted to prepare a vitamin-C 5% to 15% formulations or compositions. The solution is mixed until clear after every addition. All percentages are given by weight of final composition. All steps, except the heating step, if required, are performed at room temperature (18-25° C.).

EXAMPLE 1

Ascorbic Acid 5% (w/w):
Begin with 10.0% Demineralized water,
add 3.00% L-Ascorbic Acid (Hoffman Laroche) and begin mixing at a medium to high speed (Lightning Mixer or Agitator) add 27.35% Ethoxydiglycol Trivalin SF™,
add 2.00% Vitamin-C (Hoffman Laroche),
add 27.35% Ethoxydiglycol Trivalin SF™, add 29.00% Propylene Glycol,
add 1.00% Greentech™ Grapefruit Extract, and
add 0.3% Apple Crunch™ Fragrance,
Note: no heating is required.

EXAMPLE 2

Ascorbic Acid 10% (w/w):
Begin with 10.0% Demineralized water,
add 3.00% L-Ascorbic Acid (Hoffman Laroche) and begin mixing at a medium to high speed,
add 25.85% Ethoxydiglycol Trivalin SF™,
add 1.50% Vitamin-C (Hoffman Laroche),
add 25.85% Ethoxydiglycol Trivalin SF™,
add 3.50% Vitamin-C (Hoffman Laroche),
add 27.00% Propylene Glycol, and
add 1.00% Greentech™ Grapefruit Extract.

Heat is then applied in the formulation process. This is an important step in order to formulate a concentration of vitamin-C higher than 6% in the solution comprising 10% water. Interestingly enough, the vitamin-C does not support heat well as the latter tends to oxidize the former. However, the medium in which ascorbic acid is during heating provides protection against oxidative damage.

Therefore, a last addition of 2% Vitamin-C is performed, followed by heating to 40 degrees Celsius until the solution becomes all clear and until all vitamin-C has been dissolved.

While stirring continues, the solution is allowed to cool down at ambient temperature and then, once cooled, 0.3% Apple Crunch™ Fragrance is added.

EXAMPLE 3

Ascorbic Acid 15% (w/w):
Begin with 15.0% Demineralized water,
add 4.5% Vitamin-C (Hoffman Laroche) and being mixing at a medium to high speed,
add 23.4% Ethoxydiglycol,
add 2.25% Vitamin-C (Hoffman Laroche),
add 23.4% Ethoxydiglycol Trivalin SF™,
add 5.25% Vitamin-C (Hoffman Laroche),
add 22.0% Propylene Glycol,
add 0.09% Greentech™ Grapefruit Extract,
and 3.0% Vitamin-C (Hoffman Laroche) and heat solution to 40 degrees Celsius until solution becomes all clear and when all vitamin-C has been dissolved While stirring continues, the solution is cooled down and once cooled, 0.3% Apple Crunch™ Fragrance is added.

EXAMPLE 4

Ascorbic Acid 10% (w/w) and Hydroquinone 2% (w/w):
Begin with 12.0% Demineralized water,
add 3% Vitamin-C (Hoffman Laroche) and being mixing at a medium to high speed,
add 24.45% Ethoxydiglycol,
add 1.5% Vitamin-C (Hoffman Laroche),
add 24.45% Ethoxydiglycol Trivalin SF™,
add 3.5% Vitamin-C (Hoffman Laroche),
add 26.0% Propylene Glycol,
add 1% Greentech™ Grapefruit Extract,
and 2.0% Vitamin-C (Hoffman Laroche) and heat solution to 40 degrees Celsius until solution becomes all clear and when all vitamin-C has been dissolved.

While stirring continues, the solution is cooled down and once cooled, 0.1% Apple Crunch™ Fragrance and 2.0% hydroquinone are added.

EXAMPLE 5

Ascorbic Acid 10% (w/w) and Hydroquinone 4% (w/w):
Begin with 12.0% Demineralized water,
add 3% Vitamin-C (Hoffman Laroche) and being mixing at a medium to high speed,
add 23.45% Ethoxydiglycol,
add 1.5% Vitamin-C (Hoffman Laroche),
add 23.45% Ethoxydiglycol Trivalin SF™,
add 3.5% Vitamin-C (Hoffman Laroche),
add 26.0% Propylene Glycol,
add 1% Greentech™ Grapefruit Extract,
and 2.0% Vitamin-C (Hoffman Laroche) and heat solution to 40 degrees Celsius until solution becomes all clear and when all vitamin-C has been dissolved.

While stirring continues, the solution is cooled down and once cooled, 0.1% Apple Crunch™ Fragrance and 4.0% hydroquinone are added.

EXAMPLE 6

Ascorbic Acid 10% (w/w) and Kinetin:
Begin with 10.0% Demineralized water,
add 3% Vitamin-C (Hoffman Laroche) and being mixing at a medium to high speed,
add 25.935% Ethoxydiglycol,
add 1.5% Vitamin-C (Hoffman Laroche),
add 25.935% Ethoxydiglycol Trivalin SF™,
add 3.5% Vitamin-C (Hoffman Laroche),
add 27.0% Propylene Glycol,
add 1% Greentech™ Grapefruit Extract,
and 2.0% Vitamin-C (Hoffman Laroche) and heat solution to 40 degrees Celsius until solution becomes all clear and when all vitamin-C has been dissolved.

While stirring continues, the solution is cooled down and once cooled, 0.1% Apple Crunch™ Fragrance and 0.03% kinetin are added.

These solutions remain stable (+/−10% degradation) for approximately 24 months, which is unheard of.

FIG. 1 shows the location of the peaks of pure vitamin C. FIG. 2 shows that the maintenance of the peaks confirms that no significant degradation has occurred during the first 24 months of storage. A peak that would appear consequently to degradation is not observed in the chromatogram of the present solution.

The pH (dilution of 100 mL in water) for all 3 solutions ranges between 2.8 and 3.1.

The medium to high stirring of each ingredient added may be responsible to help form tiny water and vitamin-C spheres by "micronization" in the ethoxydiglycol/propylene glycol (both glycols) solution and because of the micronization occurring, it helps to reduce access of air which would inevitably oxidize the vitamin in the solution. It is also possible that a complex be formed between ascorbic acid and ethoxydiglycol.

EXAMPLE 7

Uses and Compositions

Therefore, the above solutions comprising a vitamin C that keeps all its integrity are intended to be used as is or through the making of a composition or a medication, to prevent or to treat any disease or disorder that involves or is caused by ROS or involving collagen synthesis. The disease or disorder includes but is not limited to skin cancer (melanoma), skin irritation or inflammation, dermatitis, skin allergy, psoriasis, acne, eczema, rosacea, radiations exposure including U.V. or sun exposure, depigmentation (skin whitening) and skin ageing (reduction of wrinkles inter alia). Compositions may comprise any suitable carrier which may include structuring agents (oils, fatty acids, surfactants, etc.) and a reducing agent or an anti-oxidant which would increase the stability of the ascorbic acid or which would complement its anti-oxidant properties. Further, compositions comprising any active ingredient which would benefit or not from the protective effect provided by vitamin C against oxidation are within the scope of the invention.

In adjunction with the present vitamin C, hydroquinone and kinetin have been used in examples provided herein to produce stabilized vitamin C compositions. The following currently used cosmetic or dermatologic products can all also be formulated in "combined" compositions: α-hydroxy acid, retinol, kojic acid, vitamin K, ascorbyl palmitate, magnesium ascorbyl phosphate and sodium ascorbyl phosphate. The combinations may include more than one of these products. The combination should remain at an acidic pH (below 7.0), and ideally below the pKa of ascorbic acid, when this pH (4.17) is compatible with the stability of the other products.

Although the present invention has been described hereinabove by way of preferred embodiments thereof, it can be modified, without departing from the spirit and nature of the subject invention as defined in the appended claims.

The invention claimed is:

1. A stabilized solution of L-ascorbic acid comprising:
   a) about 5% to about 15% (w/w) of L-ascorbic acid;
   b) about 10% to about 15% (w/w) of water;
   c) about 46.8% to about 54.7% (w/w) of ethoxydiglycol;
   d) about 22% to about 29% (w/w) of propylene glycol; and
   e) about 0.9% to about 1% of an anti-oxidant plant extract, wherein the solution has a pH of less than about 4.17.

2. The solution of claim 1, further comprising f) about 0.1% to about 0.3% of a fragrance material.

3. The solution of claim 2, wherein the fragrance material is at a concentration of about 0.2%.

4. The solution of claim 1, further comprising at least one topically suitable carrier or compound.

5. The solution of claim 4, wherein the at least one topically suitable carrier or compound comprises a topically suitable carrier or compound selected from the group consisting of tocopherol, tocopheryl acetate, retinol, retinyl palmitate, hydroquinone, proanthocyanidins, butylated hydroxytoluene, butylated hydroxyanisole, astaxanthin, alpha lipoic acid, tocotrienols, coenzyme Q10, α-hydroxy acid, kojic acid, kinetin, wine extract, vitamin K, ascorbyl palmitate, magnesium ascorbyl phosphate, sodium ascorbyl phosphate, a sun blocking agent and any combination thereof.

6. The solution of claim 4, wherein the at least one topically suitable carrier or compound comprises an additional anti-oxidant.

7. The solution of claim 6, wherein the antioxidant is at a concentration of about 0.03% to about 4%.

8. The solution of claim 7, wherein the antioxidant is at a concentration of about 0.03% to about 2%.

9. The solution of claim 1, wherein the L-ascorbic acid is at a concentration of about 10% (w/w).

10. The solution of claim 1, wherein the water is at a concentration of about 10% (w/w).

11. The solution of claim 1, wherein the ethoxydiglycol is at a concentration of about 48.9% to about 51.7% (w/w).

12. The solution of claim 1, wherein the propylene glycol is at a concentration of about 27% (w/w).

13. The solution of claim 1, wherein the anti-oxidant plant extract is at a concentration of about 1% (w/w).

14. The solution of claim 1, wherein the anti-oxidant plant extract is a grapefruit plant extract.

15. The solution of claim 1, wherein the fragrance material is an apple crunch fragrance.

16. The solution of claim 1, which comprises:
   a) about 10% of L-ascorbic acid;
   b) about 10% to about 15% (w/w) of water;
   c) about 48.9% to about 51.7% (w/w) of ethoxydiglycol;
   d) about 27% (w/w) of propylene glycol;
   e) about 1% of a grapefruit plant extract;
   f) about 0.2% of an apple crunch fragrance; and
   g) about 0.03% to about 2% of an antioxidant.

17. A topical composition comprising the solution of claim 1, and further comprising at least one topically suitable carrier or compound.

18. The topical composition of claim 17, wherein the at least one topically suitable carrier or compound comprises a topically suitable carrier or compound selected from the group consisting of tocopherol, tocopheryl acetate, retinol, retinyl palmitate, hydroquinone, proanthocyanidins, butylated hydroxytoluene, butylated hydroxyanisole, astaxanthin, alpha lipoic acid, tocotrienols, coenzyme Q10, α-hydroxy acid, kojic acid, kinetin, wine extract, vitamin K, ascorbyl palmitate, magnesium ascorbyl phosphate, sodium ascorbyl phosphate, a sun blocking agent and any combination thereof.

19. The topical composition of claim 17, wherein the at least one topically suitable carrier or compound comprises an additional anti-oxidant.

20. The topical composition of claim 17, which is a lotion or serum.

21. A process for obtaining the stabilized solution of L-ascorbic acid of claim 13, which comprises
   a) dissolving a first amount of L-ascorbic acid in water, thereby obtaining a first solution;
   b) adding a first amount of ethoxydiglycol to said first solution under a stirring speed sufficient to micronize same, thereby obtaining a second solution;
   c) adding a second amount of L-ascorbic acid to said second solution under a stirring speed sufficient to micronize same, thereby obtaining a third solution;
   d) adding a second amount of ethoxydiglycol to said third solution under a stirring speed sufficient to micronize same, thereby obtaining a fourth solution;
   e) adding a third amount of L-ascorbic acid to said fourth solution under a stirring speed sufficient to micronize same, thereby obtaining a fifth solution;
   f) adding propylene glycol to the fifth solution under a stirring speed sufficient to micronize same, thereby obtaining a sixth solution;
   g) adding the anti-oxidant plant extract to said sixth solution under a stirring speed sufficient to micronize same, thereby obtaining a seventh solution;
   h) heating the seventh solution at a temperature of about 37° C. to about 40° C.; and
   i) adding a fourth amount of L-ascorbic acid to the solution of h) under a stirring speed sufficient to micronize same.

22. The process of claim 21, wherein said temperature is about 40° C.

23. The process of claim 21, which further comprises a step j) of adding a fragrance material.

24. The process of claim 23, wherein the solution is cooled down during or after step j).

25. The process of claim 24, wherein the solution is cooled down to a temperature of about 25° C.

26. The process of claim 23, which further comprises adding at least one topically suitable carrier or compound under stirring after cooling.

27. The process of claim 26, wherein the at least one topically suitable carrier or compound comprises a topically suitable carrier or compound selected from the group consisting of tocopherol, tocopheryl acetate, retinol, retinyl palmitate, hydroquinone, proanthocyanidins, butylated hydroxytoluene, butylated hydroxyanisole, astaxanthin, alpha lipoic acid, tocotrienols, coenzyme Q10, α-hydroxy acid, kojic acid, kinetin, wine extract, vitamin K, ascorbyl palmitate, magnesium ascorbyl phosphate, sodium ascorbyl phosphate, a sun blocking agent and any combination thereof.

28. The process of claim 26, wherein the at least one topically suitable carrier or compound comprises an antioxidant.

29. A method for reducing the risks and/or symptoms of skin melanoma, skin irritation, skin inflammation, dermatitis, skin allergy, psoriasis, acne, eczema, rosacea, skin exposure to U.V., skin exposure to sun, pigmentation through skin whitening or skin ageing in a subject in need thereof, which comprises the step of topically administering to the subject a suitable amount of the solution of claim 1.

30. The method of claim 29, for reducing the risks and/or symptoms of wrinkles.

* * * * *